United States Patent [19]

Tanie et al.

[11] 4,314,379
[45] Feb. 9, 1982

[54] APPARATUS FOR DISCRIMINATION OF MYOELECTRIC POTENTIAL PATTERNS

[75] Inventors: Kazuo Tanie, Yokohama; Susumu Tachi, Tokyo, both of Japan

[73] Assignee: Agency of Industrial Science & Technology, Ministry of International Trade & Industry, Tokyo, Japan

[21] Appl. No.: 123,096

[22] Filed: Feb. 20, 1980

[30] Foreign Application Priority Data

Feb. 26, 1979 [JP] Japan .................................. 54-21645

[51] Int. Cl.³ .............................................. A61F 1/00
[52] U.S. Cl. ...................................................... 3/1.1
[58] Field of Search ............... 128/733; 3/1.1, 12–12.7

[56] References Cited

U.S. PATENT DOCUMENTS

| | | | |
|---|---|---|---|
| 4,030,141 | 6/1977 | Graupe | 3/1.1 |
| 4,170,225 | 10/1979 | Criglor et al. | 128/733 |
| 4,209,860 | 7/1980 | Graupe | 3/1.1 |

OTHER PUBLICATIONS

Costa, P.F. et al., "Multi-Channel Data Acquisition System for the Survey of Intercostal Muscle Activity", Med. & Biol. Eng. & Computers 1980 vol. 18 pp. 447–451.

Primary Examiner—Robert W. Michell
Assistant Examiner—Francis J. Jaworski
Attorney, Agent, or Firm—Kurt Kelman

[57] ABSTRACT

An apparatus for the discrimination of myoelectric potential patterns, which operates with a procedure comprising the steps of discriminantly screening instruction signals from myoelectric potential signals issuing from the subject's body, performing arithmetic operations of the linear-discriminant functions on the instruction signals against the gravity coefficients fixed in advance based on the data of average myoelectric potential patterns from the modes of motions involved, and classifying the signal of the largest value selected from the results of said arithmetic operations with respect to the prescribed mode of motion.

7 Claims, 6 Drawing Figures

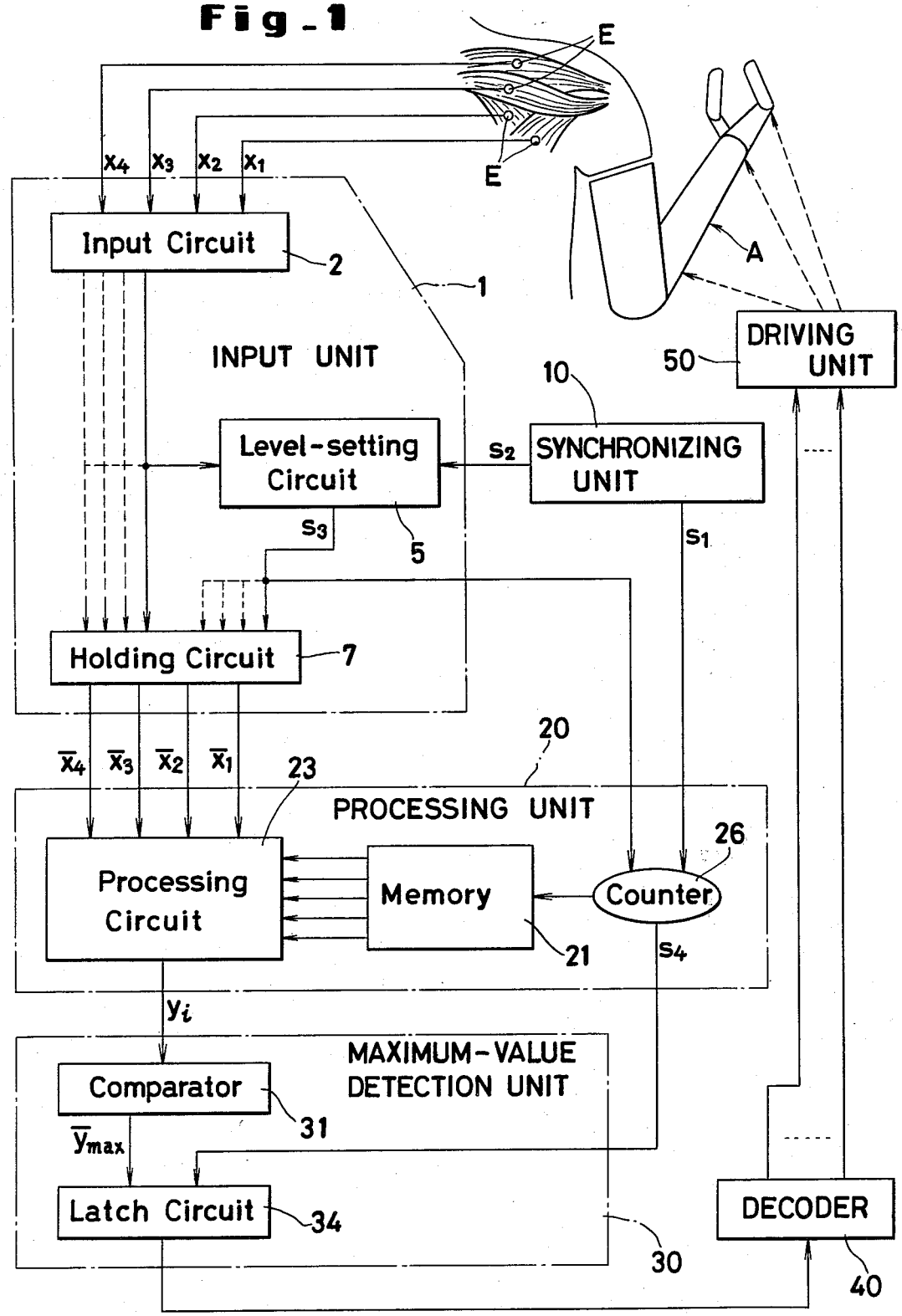

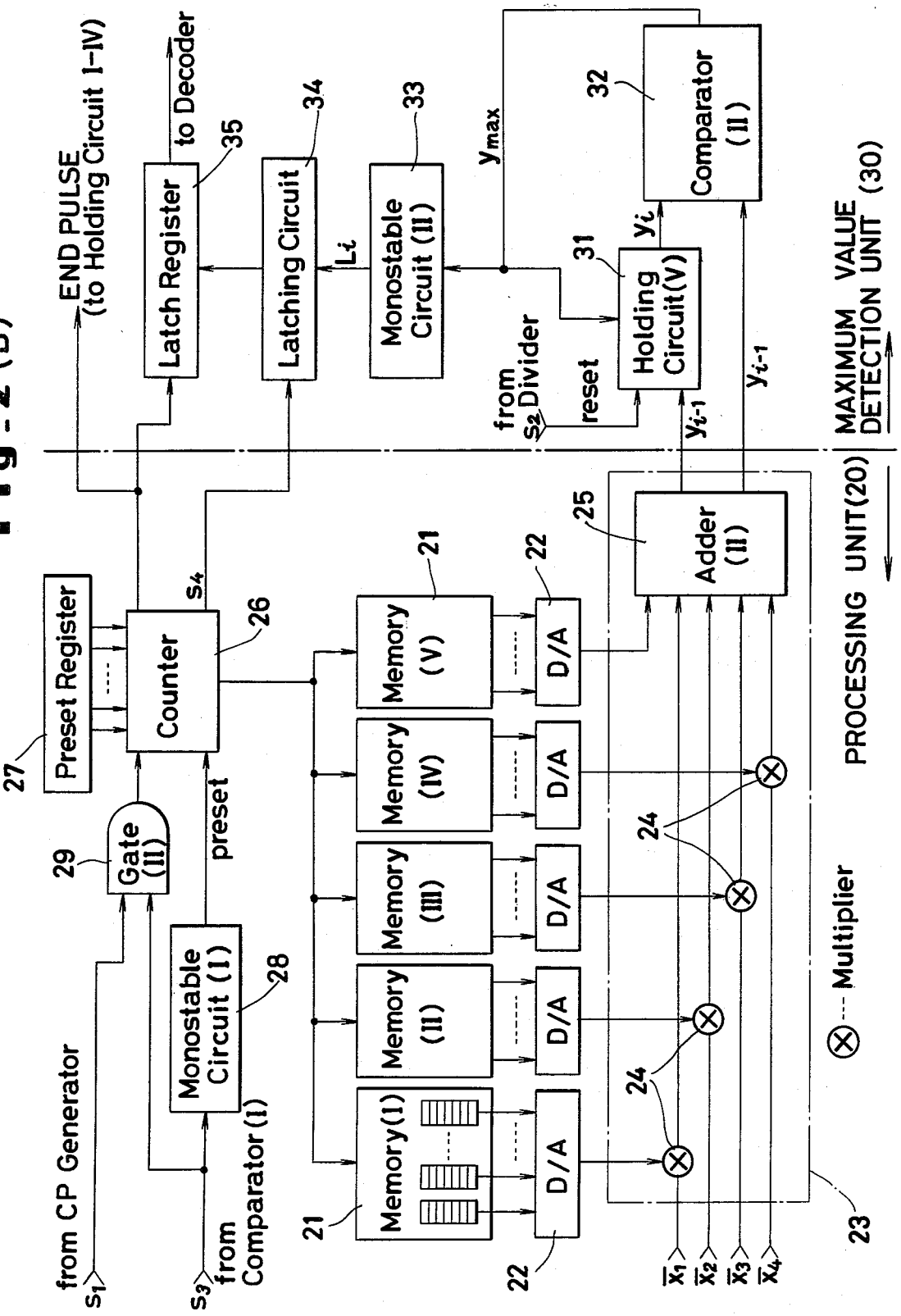

APPARATUS FOR DISCRIMINATION OF MYOELECTRIC POTENTIAL PATTERNS

BACKGROUND OF THE INVENTION

This invention relates to an apparatus for the discrimination of myoelectric potential patterns, to be used in a drive mechanism which is controlled by using, as instruction signals, various myoelectric potentials issuing from a given part of the human body.

The external-prosthesis, which aims to give relief to persons disabled by the absence of or defect in their body parts, is most advanced in the field of artificial legs and artificial arms. Artificial arms, in particular, are required to produce complicated motions. Drive mechanisms developed for operating such artificial arms by effective use of electric motors and hydraulic drive means have reached a high degree of perfection. The control of a drive mechanism, however, calls for highly complicated processing. Various methods have heretofore been proposed for the purpose of this control. Unfortunately, these methods tend to entail the common disadvantage that the control devices which embody their respective principles are unproportionately large in size for the number of modes of motions the artificial arms are expected to produce. Different methods have also been proposed for the discrimination of control signals used for causing artificial arms to produce motions. One of these methods involves use of a plurality of independent input devices and another utilizes prescribed voice sounds uttered by the user as instruction signals. All of these conventional methods are deficient, in varying measures, of the ability to provide artificial arms with perfect control devices fully satisfactory for actual use.

For a disabled person to enjoy the smoothest natural use of an artificial arm for example, the prime and sole requisite is that the entire control system should be amply small and light and it should enable the muscles in certain relevant part of the subject, such as his shoulder or remaining brachium, to issue instruction signals to the drive mechanism for the artificial arm in entirely the same manner as the above mentioned relevant part would do in moving a natural arm. The best way to fulfill this requisite resides in limiting the number of modes of motions of the artificial arm to the irreducible minimum and thereby decreasing the size and weight of the device to the fullest possible extent and using, as instruction signals for the control device, the myoelectric potentials (hereinafter referred to as "EMG") issued by the muscles of the relevant part of the subject in moving his natural arm.

Such instruction signals are effectively extracted from the muscles of the relevant part of the subject by attaching a plurality of electrodes for extracting EMG signals to as many positions around the relevant region and converting the EMG signals generated in the relevant region into a corresponding EMG pattern by means of the aforementioned extraction electrodes. Where such an EMG pattern is used as an instruction signal, a plurality of EMG patterns are generally classified on a basis of the linear discriminant principle. Methods proposed heretofore are invariably based on a principle that the control of an artificial arm is accomplished by prescribing a definite number of modes of motions the artificial arm is expeced to produce, fixing discriminant functions one each for the aforementioned different modes of motions, and providing the same number of circuits adapted to perform arithmetic operations on the discriminant functions as that of modes of motions, whereby the circuit, upon receiving incoming EMG signals, will carry out arithmetic operations on corresponding discriminant functions, compare the results of these operations with one another and single out the largest value which determines the exact motion to be imparted to the artificial arm. Devices embodying such conventional methods are required to incorporate as many circuits as there are modes of motions and, therefore, tend to make up much space. Since the discrimination devices heretofore known to the art mostly depend for the aforementioned processing of arithmetic functions upon general-purpose computers, their hardware structures take up too much space to be applied advantageously to artificial limbs.

An object of this invention, therefore, is to provide a compact apparatus for the discrimination of EMG patterns for use in a drive mechanism adapted to impart motions to an artificial limb, which apparatus extracts EMG signals issuing from a given part of a disabled person and uses them as instruction signals for the control of the drive mechanism, performs arithmetic operations on the corresponding discriminant functions at high speed and enables the artificial arm to produce smooth natural motions faithfully in response to the results of the operations.

SUMMARY OF THE INVENTION

To accomplish the object described above according to this invention, there is provided an apparatus for the discrimination of EMG patterns, which apparatus comprises an input unit for detecting EMG signals from myoelectrodes on the body of a disabled person; a processing unit provided with memories for storing the weight coefficients of discriminant functions fixed on the basis of average EMG data obtainable with the prescribed modes of motions and adapted to perform arithmetic operations successively on the EMG signals issued from the input unit and the values of coefficients from the memories in accordance with linear discriminant functions; and a maximum-value detection unit serving to single out the maximum-value signal from among the output signals from the processing unit and retain a category number signal corresponding to the maximum-value signal.

The aforementioned apparatus for the discrimination of EMG patterns, at the time that linear discriminant functions are processed, allows the EMG patterns of magnitudes each formed of a plurality of EMG signals issuing from the body to be successively subjected to arithmetic operations against each of the different modes of motions and, at the same time, compares sequentially the results of the arithmetic operations one by one. As a result, the desire to reduce the size and weight of the apparatus to the fullest possible extent is gratified. Further, this apparatus acquires an ability to preclude the possible production of erroneous motions in response to EMG signals on the noise level when the input unit is adapted to perceive as instruction signals a plurality of EMG signals only on condition that the total sum of the plurality of EMG signals surpasses the reference level. The apparatus, because of its particular configuration, permits the number of classified categories to be readily increased as required.

The other objects and characteristics of the present invention will become apparent from the further disclosure of the invention to be made hereinafter with reference to the accompanying drawing.

BRIEF EXPLANATION OF THE DRAWING

FIG. 1 is a block diagram schematically illustrating the apparatus for the discrimination of EMG patterns according to the present invention.

FIG. 2(A), FIG. 2(B) are block diagrams illustrating in detail one preferred embodiment of the apparatus for the discrimination of EMG patterns according to the present invention.

DESCRIPTION OF THE PREFERRED EMBODIMENT

Figure 2A:
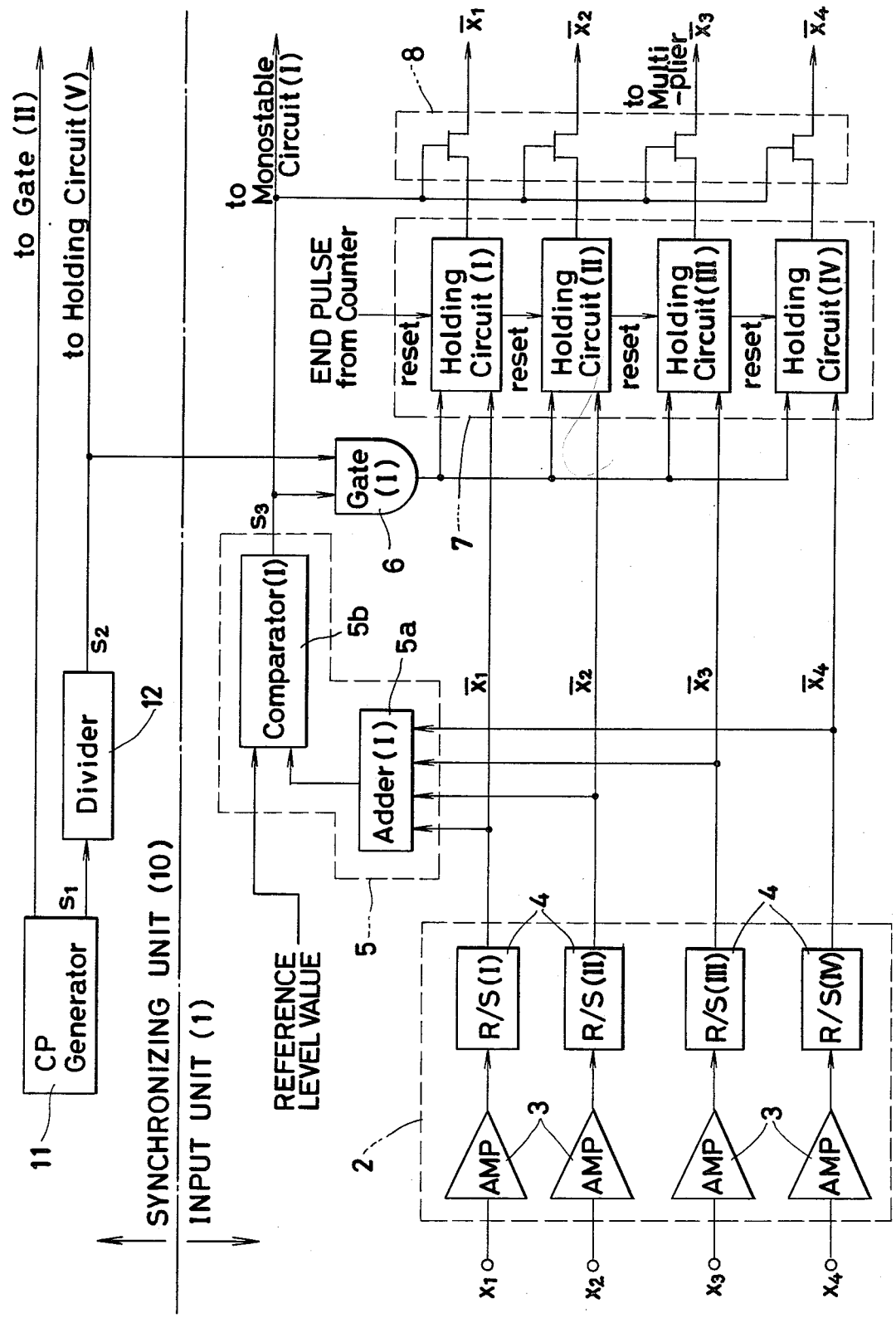

This invention relates to an apparatus for the discrimination of myoelectric potential (EMG) patterns to be used in the formation of instruction signals for the control of a drive mechanism adapted to operate by use of EMG signals.

When, for example, an artificial arm fitted to the body of a disabled person is bent and rotated at the elbow joint thereof by operating driving mechanisms which are provided at the joint, it is advantageous to utilize EMG signals in forming control signals for driving the motors as the driving mechanisms, for example. Also when the disabled person wishes to operate various mechanical implements other than his own artificial arm, it is likewise advantageous to rely upon instruction signals which are derived from such EMG signals, depending on the degree of his disability. In this case, when the mechanical implements are desired to produce numerous kinds of motions, there are inevitably required as many kinds of control signals. When the wrist and hand of the artificial arm are desired to produce motions in numerous directions by the operation of a plurality of motors disposed at the joints in the artificial arm, for example, it becomes necessary to issue widely varying control signals for designating relevant motors out of the whole group of motors available and selecting directions in which such designated motors are to be driven.

Concerning the issuance of such numerous kinds of control signals by use of EMG signals, it has been ascertained that when the EMG signals which the muscles in certain relevant regions of the human body generate in response to motions to be produced by the natural arm are detected and compared one with another against several fixed modes of motions, the EMG patterns consequently obtained with respect to the different motions vary one from another. Based on this knowledge, the present invention accomplishes the desired issuance of control signals by predetermining average EMG patterns corresponding to various modes of motions the artificial arm is expected to produce, comparing the pattern of actually extracted EMG signals with these predetermined average EMG patterns to select the preset average EMG pattern most closely approximate to the extracted EMG pattern and giving rise to a control signal corresponding to a mode of the EMG pattern selected in consequence of the comparison.

With reference to FIG. 1 which represents a block diagram of the apparatus for the discrimination of EMG patterns according to this invention, the processing function of the apparatus will be described in outline.

A plurality of electrodes E serve the purpose of extracting EMG signals. For the extraction of instruction signals from the muscular motions by the detection of changes in the EMG signals resulting from the vertical and horizontal motions produced by the clavicle in the human body, for example, the plurality of electrodes E are attached to the trapezius, the pectoralis major, the latissimus dorsi, the teres major, etc. which govern the motions of the clavicle. The present embodiment represents a case wherein control signals for n-modes of motions of the artificial are are obtained by using four electrodes. As a matter of course, the number of electrodes and the number of control signals can be freely fixed. Generally the number of control signals to be required increases in proportion as the number of modes of the motions the artificial arm is expected to produce increases. When the number of modes of the motions and that of control signals are increased, it becomes necessary to increase proportionally the number of positions of the human body used for the extraction of EMG signals and improve the fineness with which the produced EMG pattern is identified.

As the person wearing the artificial arm attempts to move the arm to a desired position, the four EMG signals reaching the electrodes E exhibit their respective magnitudes characteristic of the motion involved. Thus a pattern is formed by one set of four EMG signals. Through discrimination of the EMG pattern, there can be obtained control signals corresponding to the motion the clavicle is required to produce. These four EMG signals, $x_1$ to $x_4$, generally exhibit irregularly alternating magnitudes. They are, therefore, amplified, rectified and smoothened in the input circuit 2 of the input unit 1 to be converted into corresponding direct-current signals. These direct-current signals are held in the holding circuit 7 tobe used in the subsequent processing step.

EMG signals are generated, though very feebly, even while the issuance of control signals for the production of motions is suspended. To preclude possible production of motions by such idle myoelectric potentials, the EMG signals must be deprived of those EMG signals of the noise level before they are applied to the holding circuit 7. The elimination of those EMG signals of the noise level is effected by the level-setting circuit 5, so that only the EMG signals, $x_1$ to $x_4$, which are required for the production of motions are stored in the holding circuit 7. The EMG pattern thus obtained relative to the motions to be produced is identified by means of linear discrimination.

Classification of the patterns by the linear-discrimination method is effected as follows. As the preparatory step, the subject is caused to move his clavicle in various directions to determine in advance what EMG signals are generated, on the average, in response to the motions produced by the clavicle. This experiment is repeated many times. As a result of this experiment, category numbers, 1, ... n, are assigned one each for the different motions produced by the clavicle. The average EMG signals obtained as described above are generally called "standard patterns", which are indicated by the expression: $\bar{x}^i = (x_1^i, x_2^i, x_3^i, x_4^i)$. After completion of this preliminary experiment, the subject is again caused to move his clavicle similarly to give rise to actual input patterns $\bar{x}^a = (x_1^a, x_2^a, x_3^a, x_4^a)$. The classification of the pattern with respect to the categories mentioned above is effected by performing the calculation:

$$P^i = x^i - x^{\hat{a}} \quad (i = 1, 2, \ldots, n) \tag{1}$$

with respect to each of the different categories, comparing the terms, $\bar{P}_1, \ldots, \bar{P}_n$ corresponding to the n-categories, to single out $\bar{P}_l$ ($1 \leq l \leq n$) as the term having the smallest value and concluding that the pattern in question belongs to Category 1. The classification of Formula (1) indicated above is generally considered to be equivalent to the classification which comprises carrying out the calculation of the array of linear functions shown below with respect to the input pattern ($x_1^\alpha$, $x_2^\alpha$, $x_3^\alpha$, $x_4^\alpha$) and finding the term $y_l$ having the maximum value to which the caterogy 1 corresponds.

$$\begin{aligned} y_1 &= a_{1,1}x_1^\alpha + a_{1,2}x_2^\alpha + a_{1,3}x_3^\alpha + a_{1,4}x_4^\alpha + a_{1,5} \ldots \text{①} \\ y_2 &= a_{2,1}x_1^\alpha + a_{2,2}x_2^\alpha + a_{2,3}x_3^\alpha + a_{2,4}x_4^\alpha + a_{2,5} \ldots \text{②} \\ &\vdots \\ y_n &= a_{n1}x_1^\alpha + a_{n2}x_2^\alpha + a_{n3}x_3^\alpha + a_{n4}x_4^\alpha + a_{n5} \ldots \text{ⓝ} \end{aligned} \tag{2}$$

In the formula given above, $a_{ij}$ ($i = 1, 2, \ldots, n$, $j = 1, 2, \ldots, 5$) represents a constant (weight coefficient) to be determined by this value of the standard pattern.

In the processing unit indicated in the diagram of FIG. 1, the calculation of the righthand side of the equation of Formula (2) is carried out. These calculations of function are not carried out all at once but are performed one by one in accordance with the clock generated by the synchronizing unit 10.

In the processing unit 20, the weight coefficients are set in the memories 21 and are successively subjected to arithmetic operation in the processing circuit 23, with the result that signals $y_i$ are successively issued through synchronization with the clock.

The signals $y_i$ issued from the processing unit 20 are received in the subsequent maximum-value detection unit 30, in which the particular category number corresponding to the signal $y_{max}$ having the maximum value is singled out. It is forwarded through the decoder 40 to the artificial arm A and used for the selection of the mode for the motion of the artificial arm. Now, the operation of the apparatus will be described in detail with reference to FIGS. 2(A) and 2(B).

Figure 3:
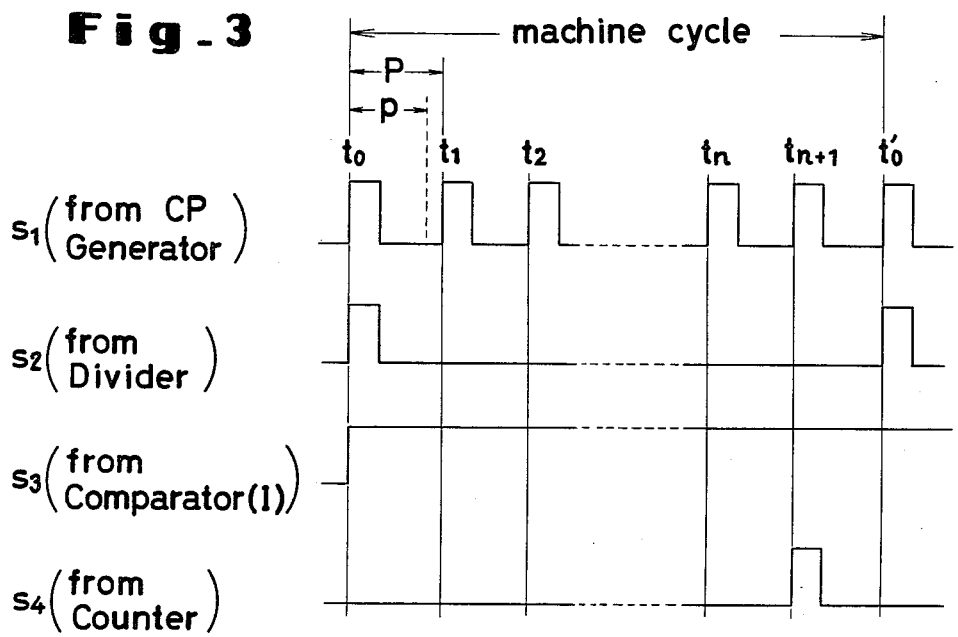
FIG. 3 is a time chart concerning the operations of the component units as indicated in FIG. 2.

FIG. 2(A) is a detailed block diagram of the input unit 1 (lower side) and the synchronizing unit 10 (upper side). From the clock-pulse (CP) generator 11 of the synchronizing unit 10, a pulse train $s_1$ with a pulse separation P as shown in FIG. 3 is issued. This pulse serves as the standard pulse for the calculation performed with respect to each of n-discriminant functions. The pulse separation P is fixed so as to satisfy $P > p$ wherein p denotes the operation time, namely the length of time required for the performance of the abovementioned calculation of one discriminant function. In the meantime, the EMG signals extracted by the electrodes from the different positions are amplified by the myoelectric amplifiers 3, then rectified and smoothened by the rectifying and smoothening (R/S) circuits 4 and, consequently, converted into direct-current signals $\bar{x}_m$. They are subsequently held in the holding circuits (I)–(IV) until all the calculations of the discriminant functions of Formula (2) are completed. The hold signal $s_2$, as illustrated in FIG. 3, is a signal obtained by dividing the output $s_1$ from the CP generator 11 by the frequency divider 12. The hold signal is issued once for each machine cycle. This signal $s_2$ assumes a length of time which is (n+1) times the length of the pulse separation P.

It is imperative that before they are subjected to the arithmetic operations by the apparatus of this invention, the EMG signals issued from the muscles in consequence of the motions produced by the clavicle should be examined to determine whether or not they constitute control signals for the artificial arm. For the purpose of this particular examination, the apparatus of this invention is provided with a level-setting circuit 5, which is adapted to permit the processing for the calculation of the discriminant functions only when the total sum of the rectified and smoothened values of all the EMG signals exceeds a fixed level. Specifically with reference to FIG. 2(A), the aforementioned examination is accomplished by summing the output values from the R/S circuits 4 in the adder(I) 5, comparing the resultant sum of output values with the reference-level value preset in the comparator(I) 5b, opening the gate 6 only when the output of the comparator(I) is ON, enabling the output of the frequency divider 12 to be delivered to the hold circuit, and retaining the EMG signals. The signal $s_3$ shown in FIG. 3 is the output from the comparator(I) 5b.

Figure 4:
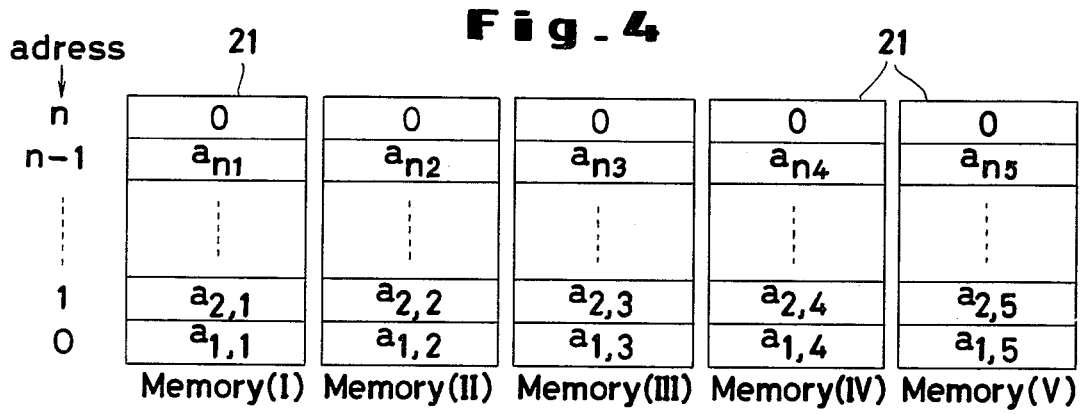
FIG. 4 is a schematic diagram illustrating the state of coefficients stored in the memories of FIG. 2(B).
Figure 5:
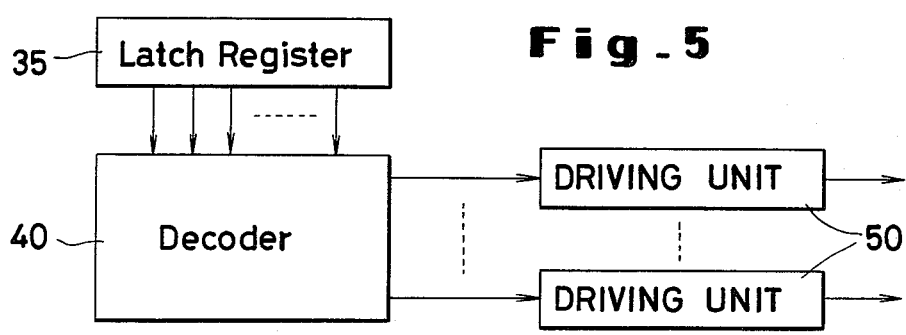
FIG. 5 is a block diagram illustrating the function of the decoder to be used in one preferred embodiment of this invention.

When a motion of some form or other is produced and the total sum of EMG signals consequently generated exceeds the aforementioned level, the gate(I) 6 is opened and the hold signal is issued synchronously with the signal $s_2$ from the divider 12 to hold the EMG signals from the R/S circuits 4. At the same time, the analog switch 8 is opened by the output of the comparator(I) 5b and the EMG signals are applied to the multipliers 24 of the processing circuit 23 shown in FIG. 2(B). To the remaining input terminals of these multipliers 24 are delivered, through the digital-to-analog converters (D/A) 22, the outputs from the memories(I)–(IV) 21 which keep the weight coefficients of discriminant functions in the form of digital numerals as shown in FIG. 4. The result is that the operation of the multipliers 24 gives rise to the products of the rectified and smoothened values of EMG signals ($\bar{x}_1$, $\bar{x}_2$, $\bar{x}_3$, $\bar{x}_4$) and the coefficients ($a_{i1}$, $a_{i2}$, $a_{i3}$, $a_{i4}$, $a_{i5}$). The coefficients in the memories(I)–(V) 21 are successively delivered to the multipliers 24 in accordance with the timing of the output of the CP generator 11 when the remaining gate(II) 29 is ON. In this timing, the value "n" (the number of discriminant functions) corresponding to the number of categories involved in the classification is set in advance in the preset register 27 and the content in the preset register 27 is transferred via the gate(II) 29 into the counter 26 by order of the pulse obtained by processing the leading of the output of the comparator(I) 5b in the monostable circuit(I) 28. When the content of the counter 26 is decreased by one for each pulse $s_1$ of the output from the CP generator 11, the content of the counter becomes $n-1$ and, consequently, the address $n-1$ in the memories(I)–(V) is designated as illustrated in FIG. 4. The result is that the contents ($a_{n1}$, $a_{n2}$, ... $a_{n5}$) of the memories are transferred via the D/A converters 22 into the multipliers 24. The contents of the counter 26 are decreased to $n-2$, $n-3$, ... 0 as the 2nd, 3rd, ... output pulses are issued from the CP generator 11. Consequently, the contents $(a_{n-1,1}; a_{n-1,2}; \ldots a_{n-1,5}) \ldots (a_{1,1}; a_{1,2}; \ldots a_{1,5})$ of the memories(I)–(V) at the addresses $n-2, n-3, \ldots 0$ are successively delivered to the multipliers 24.

The output of the multipliers 24 is then fed to the adder(II) 25. This means that the signals $y_1$ to $y_n$ are calculated, as synchronized with the pulse from the CP generator 11, in the order of $y_n, y_{n-1}, \ldots y_1$ in accordance with ⑬ to ① of Formula (2). The outputs $y_i$ ($i = 1, 2, \ldots, n$) are further applied successively to the maximum-value detection unit 30. The content of the holding circuit(V) 31 is reset to the level 0 by the signal $s_2$ of the divider 12 as illustrated in FIG. 3. Also, the output level of the maximum-value detection unit 30 is maintained at the level 0 when the input remains at the level 0. When the outputs $y_i$ from the adder(II) 25 are fed into the maximum-value detection unit 30 synchronously with the clock pulse, they are compared by the comparator-(II) 32 with the outputs from the holding circuit(V) 31 (the output 0 where $i = 1$). When $y_i$ is greater than 0, the output $y_{max}$ of the maximum-value detection unit assumes the status of ON. Consequently, the monostable circuit(II) 33 is driven to issue the latch signal $L_i$ to the latch circuit 34. At the same time, the signal is fed back to the holding circuit(V) 31 to hold the output $y_i$. On receiving this latch signal $L_i$, the latch circuit 34 latches at that moment the content of the counter 26 corresponding to the number of the categories, namely the signal $i-1$. As the next clock pulse is issued from the CP generator 11 and the output $y_{i-1}$ from the processing unit 20 is calculated by the aforementioned procedure and then forwarded to the maximum-value detection unit, the output $y_i$ and the output $y_{i-1}$ are compared in the state as illustrated in FIG. 2(B) because, at this stage, the output $y_i$ is held in the holding circuit(V) 31. If the output $y_{i-1}$ is greater than the output $y_i$, the signal of $i-2$ is latched in the latch circuit 34 and the output $y_{i-1}$ is held in the holding circuit(V) 31 and, thereafter, the issuance of the output $y_{i-2}$ by the subsequent clock pulse is awaited. If the output $y_{i-1}$ is smaller than the output $y_i$, the existing status is left unchanged and the issuance of the next value from the adder(II) is awaited. When the outputs $y_n$ to $y_l$ are successively compared, the value resulting from the subtraction of 1 from the number "i" corresponding to the i'th signal designating the maximum value $y_{max}$ among the outputs $y_n$ to $y_l$ will eventually remain in the latch circuit 34.

The content of the counter 26 is successively decreased by one for each pulse issued from the CP generator 11. When the content of the counter 26 is lowered below 0 by the $(n+1)$th subtractive pulse, namely when all the comparisons of the outputs $y_l$ to $y_n$ are completed, the borrow signal $s_4$ is issued by the timing illustrated in FIG. 3. By this borrow signal, the content of the latch circuit 34 is forwarded to the latch register 35 and latched therein and, at the same time, with the issuance of END PULSE, the contents of the holding circuits(I)–(IV) 7 are also cleared. In the latch register 35 is stored the value which is obtained by subtracting 1 from the category number corresponding to the signal having the maximum value among the outputs $y_1$ to $y_n$. Thereafter, upon the arrival of the subsequent clock pulse generated by the CP generator at $t_o'$ time, the same operation is repeated when the EMG signals are in their active state. As a result, the data corresponding to the category number having the maximum value in the discriminant function are issued as the output from the latch register 35 by the machine cycle of $(n+1)P$. The content to be stored in this latch register 35 is similar in form to the signal which is held in the counter 26. For this content to be converted into the control signal for the artificial arm, the output from the register 35 is decoded by the decoder 40. The control signal thus produced is sent to the driving unit 50 adapted to operate the drive mechanisms corresponding to the joints in the artificial arm.

As described above, the apparatus of the present invention enjoys perfect freedom from possible erroneous operation by passing feeble EMG signals through the level-setting circuit of the input unit 1 and discriminating instruction signals precisely from noise signals and warrants quick and accurate performance by having weight coefficients stored in memories and then subjected to DA conversion and thereby permitting analog processing of discriminant functions. Alteration of weight coefficients can be very easily effected by revision of the contents of memories. Further the fact that the arithmetic operations on the different formulas involving discriminant functions are sequentially carried out and the results of the operations are successively compared enables the apparatus of this invention to provide efficient processing of data and, at the same time, permits the apparatus to function effectively with an extremely small number of circuit elements and occupy a very small space. Moreover, this invention can be applied to the control of the other artificial limbs and other ordinary machine tools besides the control of artificial arms.

What is claimed is:

1. An apparatus for the discrimination of myoelectric potential patterns obtained by m myoelectric potential signals derived from motions of muscles of a body part and transmitted by a plurality of myoelectrodes fastened to the muscles at a like plurality of positions, the myoelectric potential patterns having n categories each one of which is assigned to a different motion produced by the muscles, the apparatus comprising an input unit for rectifying and smoothing the myoelectric
  potential signals transmitted by the myoelectrodes, means for summing said potential signals and for comparing the sum of the transmitted myoelectric potential signals with a preset reference level and, when the sum exceeds the reference level, forwarding the individual myoelectric potential signals through an output of the input unit;
  a processing unit formed of a group of memories having stored therein the weight coefficients determined on the basis of the average myoelectric potential patterns obtained in advance with prescribed modes of motions of the muscles and a processing circuit for performing one by one arithmetic operations on the actual myoelectric potential signals (s) received from the output of said input unit, wherein denotes actual input patterns, and the weight coefficients (a) from the memories in accordance with linear discriminant functions expressed by the following formulas to issue values (y) successively:

$$y_1 = a_{1,1}x_1^\alpha + a_{1,2}x_2^\alpha + \ldots + a_{1,m}x_m^\alpha + a_{1,m+1}$$
$$y_2 = a_{2,1}x_1^\alpha + a_{2,2}x_2^\alpha + \ldots + a_{2,m}x_m^\alpha + a_{2,m+1}$$
$$\vdots$$

-continued
$$y_n = a_{n,1}x_1^a + a_{n,2}x_2^a + \ldots + a_{n,m}x_m^a + a_{n,m+1}$$

wherein n is the number of the categories of the modes of the motions and m is the number of the myoelectric potential signals;

a maximum-value detection unit for latching the signal of the maximum value singled out of the values received from the processing unit and issuing, as output, the signal of the category number corresponding to the maximum-value signal; and a synchronizing unit for synchronizing the operation of the input unit, processing unit and maximum-value detection unit.

2. The apparatus according to claim 1, wherein the input unit comprises amplifiers for amplifying the myoelectric potential signals from the myoelectrodes; rectifying and smoothening circuits for causing the amplified signals from said amplifiers to be rectified and smoothened; a level-setting circuit formed of an adder for summing all the output signals from said rectifying and smoothening circuits and a comparator serving to compare the total-sum signal from the adder with the reference level and, when said total-sum signal exceeds the reference level, discharge the signal as the output; a gate serving to permit passage of the synchronizing signal from said synchronizing unit by using, as the trigger signal, the output from said comparator; holding circuits for receiving and holding the output signals from said rectifying and smoothening circuits by virtue of said synchronizing signal passing said gate; and an analogue switch serving to permit passage of the signal held in said holding circuits upon receiving the output from the level-setting circuit.

3. The apparatus according to claim 1, wherein the weight coefficients to be stored in the memories of the processing unit are in the form of digital numerals and digital-analogue converters are interposed one each between said processing circuit and said memories.

4. The apparatus according to any of claims 1, 2 or 3 wherein said processing circuit of said processing unit each comprise a plurality of multipliers and an adder and cause the coefficients to be multiplied in said multipliers by the variables of myoelectric potential data for the purpose of calculating said linear discriminant functions and cause the products of said multiplication to be totalled in said adder.

5. The apparatus according to claim 1, wherein said maximum-value detection unit comprises a comparator serving to receive successively the values obtained by the arithmetic operations in said processing unit and, when newly received values are greater than formerly received values, forward said newly received values as the output; holding circuits serving to effect a holding operation upon receiving the signal from the comparator, hold the signal of larger values and, at the next clock timing, release the retained signals back to the comparator; a latching circuit for latching the category-number signals of the modes of motions corresponding to the output signals from the comparator; and a latch register serving to receive the category-number signals from the latching circuit after completion of the operation and discharge said category-number signals as the output.

6. The apparatus according to claim 1 or claim 5, wherein said processing unit is provided with a counter and a preset register for delivering numeral signals to said counter upon start of the machine cycle and, therefore, is enabled to reading of said memories by the counter in accordance with the synchronizing signals from said synchronizing unit and produce the category-number signal to be forwarded to said maximum-value detection unit by decreasing the numeral signals received from the preset register for each synchronizing signal being received.

7. The apparatus according to claim 1, or claim 5 which further comprises a decoder for decoding the category-number signals from said maximum-value detection unit and discharge corresponding control signals as the output.

* * * * *